United States Patent
Gupta et al.

(10) Patent No.: US 8,388,887 B2
(45) Date of Patent: Mar. 5, 2013

(54) METHODS FOR MAKING TEXTURED CERAMIC IMPLANTS

(75) Inventors: Gautam Gupta, Warsaw, IN (US); Daniel Norton, Indianapolis, IN (US); Derek King, Liberty, MO (US)

(73) Assignee: Biomet Manufacturing Corp., Warsaw, IN (US)

( * ) Notice: Subject to any disclaimer, the term of this patent is extended or adjusted under 35 U.S.C. 154(b) by 346 days.

(21) Appl. No.: 12/758,503

(22) Filed: Apr. 12, 2010

(65) Prior Publication Data

US 2011/0251698 A1 Oct. 13, 2011

(51) Int. Cl.
*B28B 3/10* (2006.01)
(52) U.S. Cl. ........................................................ 264/667
(58) Field of Classification Search .................... 264/667
See application file for complete search history.

(56) References Cited

U.S. PATENT DOCUMENTS

| | | | |
|---|---|---|---|
| 4,786,555 A | 11/1988 | Howard, Jr. | |
| 5,055,318 A * | 10/1991 | Deutchman et al. | 427/534 |
| 5,263,986 A * | 11/1993 | Noiles et al. | 623/23.55 |
| 5,405,389 A * | 4/1995 | Conta et al. | 623/23.55 |
| 5,429,647 A * | 7/1995 | Larmie | 51/295 |
| 5,498,269 A * | 3/1996 | Larmie | 51/295 |
| 5,551,963 A * | 9/1996 | Larmie | 51/307 |
| 5,645,593 A * | 7/1997 | Woods et al. | 623/23.5 |
| 5,658,333 A * | 8/1997 | Kelman et al. | 623/23.6 |
| 6,090,999 A * | 7/2000 | Bruce et al. | 606/300 |
| 6,206,924 B1 | 3/2001 | Timm | |
| 6,277,295 B1 | 8/2001 | Sarkar et al. | |
| 6,287,341 B1 | 9/2001 | Lee et al. | |
| 6,682,567 B1 | 1/2004 | Schroeder | |
| 6,695,967 B2 | 2/2004 | Bishop et al. | |
| 6,953,594 B2 | 10/2005 | Lee et al. | |
| 6,972,130 B1 | 12/2005 | Lee et al. | |
| 7,413,753 B2 | 8/2008 | Li et al. | |
| 7,445,640 B2 | 11/2008 | Despres, III et al. | |
| 7,482,390 B2 | 1/2009 | Johnson et al. | |
| 7,517,539 B1 | 4/2009 | Lee et al. | |
| 7,635,447 B2 | 12/2009 | Hamman et al. | |
| 7,883,661 B2 | 2/2011 | Hamman et al. | |
| 2002/0136696 A1 | 9/2002 | Lee et al. | |
| 2005/0281999 A1 | 12/2005 | Hofmann et al. | |
| 2006/0241776 A1 | 10/2006 | Brown et al. | |
| 2006/0241781 A1 | 10/2006 | Brown et al. | |
| 2007/0129809 A1 | 6/2007 | Meridew et al. | |

(Continued)

FOREIGN PATENT DOCUMENTS

| | | |
|---|---|---|
| EP | 1290992 | 3/2003 |
| EP | 1820475 | 8/2007 |
| WO | WO2006/007861 | 1/2006 |

*Primary Examiner* — Jason L Lazorcik
*Assistant Examiner* — Russell Kemmerle, III
(74) *Attorney, Agent, or Firm* — Harness, Dickey

(57) ABSTRACT

A ceramic implant having a rough surface texture and a method for forming the same. The method includes forming a green body of a first ceramic composition. The green body is reduced to smaller pieces thereby forming ceramic fragments. A mold is filled with a second ceramic composition to form a ceramic base. Ceramic fragments are added to the mold and an outer layer is formed over at least a portion of the ceramic base. Pressure is applied to the mold to compress the outer layer onto the ceramic base and to form a green assembly. The green assembly is sintered to form a ceramic implant having a rough surface texture.

20 Claims, 2 Drawing Sheets

U.S. PATENT DOCUMENTS

| | | |
|---|---|---|
| 2007/0173948 A1 | 7/2007 | Meridew et al. |
| 2008/0114468 A1 | 5/2008 | Kumar |
| 2008/0147187 A1 | 6/2008 | Bollinger et al. |
| 2008/0208353 A1 | 8/2008 | Kumar et al. |
| 2009/0254191 A1 | 10/2009 | Despres, III et al. |
| 2010/0004754 A1* | 1/2010 | Brown et al. .............. 623/22.32 |
| 2010/0047434 A1 | 2/2010 | Kumar |
| 2011/0143127 A1* | 6/2011 | Gupta et al. .................. 428/336 |

* cited by examiner

METHODS FOR MAKING TEXTURED CERAMIC IMPLANTS

The present technology relates to ceramic medical implants provided with a porous or textured feature, and methods of their manufacture.

In the growing field of medical devices, there is a continued need to provide lightweight orthopedic implants having enhanced strength, such as implants with a porous portion or rough surface texture that can provide a three-dimensional space for bone in-growth capability. Implants having rough surface textures may facilitate enhanced in-growth and additionally provide or otherwise increase micromechanical stability and the potential for subsequent chemical bonding. Ceramic materials are desirable for their long wear characteristics, reduction in wear debris, high hardness, and low coefficient of friction. Commonly used processes to create rough surface textures, such as grit blasting or surface etching, cannot typically be applied to ceramic materials because they may lead to strength reduction and grain boundary cavitations that would negatively impact overall mechanical performance. Thus, although ceramic and ceramic-containing implants have many advantages, there remains a need to additionally provide porous or textured surfaces while minimizing cracks, crack propagation, and prevent strength reduction in order to provide enhanced implants.

SUMMARY

The present technology provides a ceramic-containing implant. In various embodiments, the implant includes a ceramic base. An outer layer is formed over or otherwise contacts a surface of the ceramic base and yields a rough outer surface. The outer layer may comprise ceramic fragments having substantially the same chemical composition as the ceramic base. In certain embodiments, the ceramic fragments are selected having a size distribution wherein about 75 wt % of the fragments have a diameter from about 0.5 mm to about 2 mm and about 25 wt % of the fragments have a diameter from about 2 mm to about 5 mm.

The present technology also provides methods for forming a ceramic implant having a rough surface texture. In various aspects, the method includes forming a green body of a first ceramic composition. The green body is reduced to smaller pieces thereby forming ceramic fragments. A mold is filled with a second ceramic composition to form a ceramic base. Ceramic fragments are added to the mold such that an outer layer is formed over a surface of the ceramic base. Pressure is applied to the mold to compress the outer layer onto the ceramic base and to form a green assembly. The green assembly is sintered to form a ceramic implant having a rough surface texture.

In another embodiment, the method includes filling a mold with a ceramic composition and applying pressure to the mold to compress the ceramic composition, thereby forming a green ceramic base. At least a portion of the green ceramic base is plasma spray coated with a ceramic powder forming a porous outer layer. The coated green ceramic base is then sintered to form a ceramic implant having a rough surface texture.

DRAWINGS

It should be noted that the figures set forth herein are intended to exemplify the general characteristics of materials, methods and devices among those of the present technology, for the purpose of the description of certain embodiments. These figures may not precisely reflect the characteristics of any given embodiment, and are not necessarily intended to define or limit specific embodiments within the scope of this technology.

DETAILED DESCRIPTION

The following description of technology is merely exemplary in nature of the subject matter, manufacture and use of one or more inventions, and is not intended to limit the scope, application, or uses of any specific invention claimed in this application or in such other applications as may be filed claiming priority to this application, or patents issuing therefrom. A non-limiting discussion of terms and phrases intended to aid understanding of the present technology is provided at the end of this Detailed Description.

The present technology relates to methods for improving the strength and in-growth capability of medical implants. As used herein, the term "implant" may be used to refer to an entire implant, or a portion thereof. For example, an implant made in accordance with the present technology, generally including a ceramic base with an outer layer including ceramic fragments, may constitute the entire implant, or it may be used with one or more pieces or components that together form a final implant or implant assembly. Accordingly, one or more portions of the implant may be provided with a ceramic base and outer layer, or the entire implant may be defined by a ceramic base having an outer layer. As such, the present technology encompasses a wide variety of therapeutic and cosmetic applications, in human or other animal subjects, and the specific materials and devices used must be biomedically acceptable. As used herein, such a "biomedically acceptable" component is one that is suitable for use with humans and/or animals without undue adverse side effects (such as toxicity, irritation, and allergic response) commensurate with a reasonable benefit risk/ratio.

Figure 1:
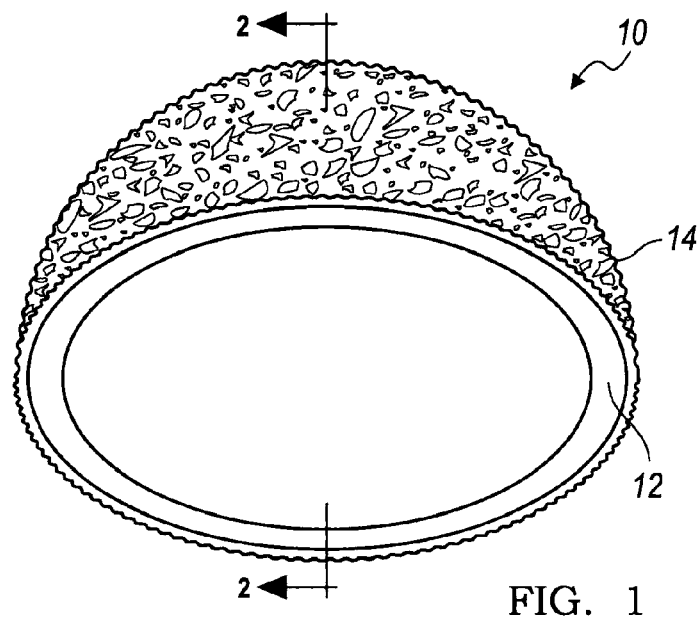
FIG. 1 is a perspective view of an exemplary acetubular cup shaped ceramic implant having a textured surface coating.

The present technology provides for a ceramic-containing medical implant and methods for forming a ceramic-containing implant having a rough or porous surface texture. FIG. 1 illustrates an exemplary acetubular cup or shell-type medical implant 10 having a ceramic base 12 with an outer layer 14 formed, covering or otherwise in contact with a surface of the ceramic base 12. The outer layer may be uniform, or may not cover the entirety of the surface on which it is formed. In various embodiments, the outer layer is in contact with the entire surface of the ceramic base. In other embodiments, the outer layer covers only a portion of the surface of the ceramic base.

Figure 2:
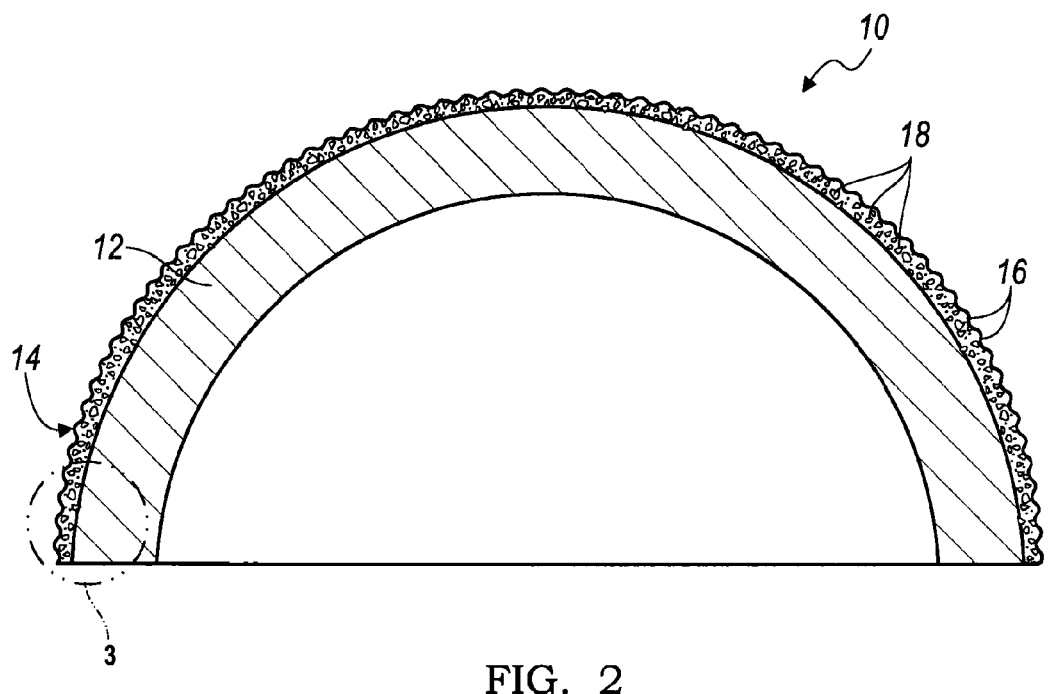
FIG. 2 is a cross sectional view of FIG. 1 taken along the line 2-2.
Figure 3:
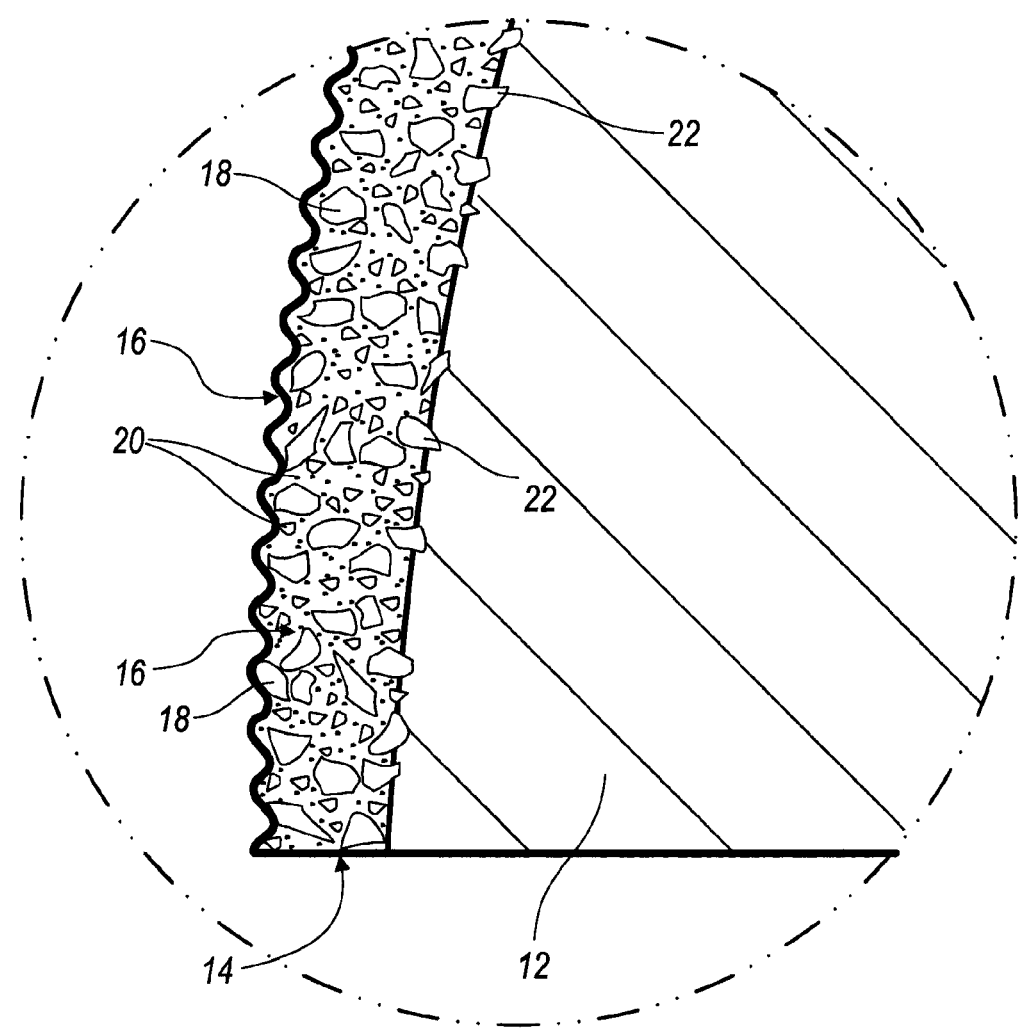
FIG. 3 is a magnified view of a portion of the implant and illustrates one embodiment of a textured surface coating.

FIG. 2 is a cross-sectional view of FIG. 1, taken along the line 2-2, and FIG. 3 is a magnified view of a portion of FIG. 2. The outer layer 14 may comprise ceramic fragments 18, 22 that may have substantially the same chemical composition as the ceramic base 12, as will be discussed below. The outer layer 14 may form a rough outer surface having numerous exposed pores, or voids 16, certain of which face the exterior to allow for bone-ingrowth and other benefits. In various aspects, the outer layer 14 may comprise a ceramic composition in addition to the ceramic fragments 18, 22. Such a ceramic composition may include smaller ceramic particles 20, optionally including a ceramic powder, disposed within certain of the spaces or voids 16 between the ceramic fragments 18, 22. In various aspects, such smaller particles 20 or powder may be provided of selected quantity and having selected size and shape, so as to create and to adjust the overall porosity of the outer layer 14 or to increase the strength and stabilization. As shown in FIG. 3, the ceramic fragments 18, 22 may have random overall shapes, sizes, and geometries. Depending on the method of forming the outer layer, as will be detailed below, and depending on the physical properties of the ceramic base 12, certain of the ceramic fragments 22 or particles 20 of the outer layer 14 may be partially or fully embedded or pressed into the ceramic base 12. Accordingly, in certain embodiments, there may not be a well-defined border between the outer layer 14 and the ceramic base 12.

The implants of the present technology comprise a ceramic base, which may comprise one or more ceramic materials as well as optional non-ceramic materials. Ceramics used in the implants of the present technology can be made of any suitable biomedically acceptable ceramic material. Generally, such ceramic materials include inorganic, non-metallic materials that are processed or consolidated at a high temperature. Suitable ceramic powders may include structural ceramics, as opposed to ceramic powders that are resorbable, for example, hydroxyapatite and calcium phosphate. Suitable structural ceramic materials may be prepared from a variety of materials, including ceramics that are known in the art, including any one or more ceramic oxides or non-oxides, such as carbides, borides, nitrides, sulfides, and silicides. Particular oxides may include alumina and zirconia as well as titanium oxide and titanium dioxide. Zirconia can be chemically "stabilized" in several different forms, including magnesia-stabilized zirconia, calcium oxide stabilized zirconia, and yttria-stabilized zirconia. Particular non-oxides may include silicon nitride and silicon carbide, or metal nitride and metal carbide. Doped ceramics may also be used, such as yitria, magnesium oxide, strontium oxide, alumina, and combinations thereof.

The methods of the present technology typically begin with a forming step. Ceramic medical devices are generally made by first forming raw ceramic materials into shapes that are loosely held together. In the art, such a loosely held together shape is commonly known as a "green body." Accordingly, the use of "green" as a modifier in the present disclosure refers to raw, or unsintered, shaped, pressed, or loosely held together ceramic composition(s), ceramic material(s), or mixtures thereof. Green bodies may be formed by various means including casting, compaction in a suitable die under isostatic pressure, compaction on the surface of a substrate, extrusion, immersion, spraying, and injection molding.

In various aspects, the ceramic materials used in the methods and compositions of the present technology may comprise a dry, finely divided ceramic powder. The ceramic composition may also comprise additional dry materials and additives. In addition, or alternatively, the ceramic composition may comprise a damp powder or a ceramic slurry made using either aqueous or organic liquid. A damp powder or slurry may further comprise additional materials and additives, for example a binder or solvent. In certain aspects, the implant of the present technology includes a homogeneous ceramic composition, while in other aspects, the implant may include a mixture of two or more different ceramic compositions.

The ceramic composition may comprise a ceramic slurry including a ceramic powder and a solvent. Ceramic slurries may be produced by any suitable means, including those known in the art. For instance, a slurry may be produced by mixing a ceramic powder with a liquid solvent, whereby the ceramic particulates are suspended in the liquid. Suitable solvents can comprise one or more polar or non-polar liquids, including liquids such as water, aqueous solutions, acetone, alcohols, organic solvents, and halogenated solvents. Alcohols may include $C_1$-$C_8$ alcohols, such as ethyl alcohol, butyl alcohol, isopropyl alcohol, and the like. Organic solvents may include aromatic solvents, such as toluene and the like. Suitable halogenated solvents may include chlorinated solvents such as methylene chloride, tetrachloromethane, and the like.

A liquid solvent may be capable of vaporizing at ambient or non-sintering temperatures prior to consolidation or sintering, or at the temperatures reached during sintering of the ceramic medical devices of the disclosure. The polarity of the solvent can be chosen based on the solubility characteristics of other slurry materials. For example, a solvent may be chosen such that space fillers, if present, do not dissolve in the solvent.

Binders may also be included in the ceramic slurry of the disclosure. Binders can be used to increase the cohesiveness of a ceramic composition. Binders may decompose into volatile and/or gaseous residues, or oxidize at or below the temperature at which sintering occurs. Suitable binders can include organic materials with a melting point of less than about 300° C. Suitable organic binders may be hydrocarbon polymers that decompose at the high temperatures associated with the sintering process. Nonlimiting examples of suitable organic binders include waxes (for instance paraffin wax), polyethylene glycol, polyvinyl alcohol, carboxymethyl cellulose, and combinations thereof.

A ceramic slurry can comprise additional additives. Nonlimiting examples of additional additives include molding adjuvants such as dispersion agents, antifoamers (for example 1-butanol), and antistatic agents. It should be understood however, that the optional use of binders, solvents, additives, etc. may not be desirable for certain embodiments because of the risk of potential contamination of the ceramic.

In the case of casting, a ceramic slurry may be cast in a mold according any method known in the art. Casting of ceramics may be performed at room temperature. A green body may be cast and then sintered, wherein solvent and any binder and/or nondissolving filler is vaporized, oxidized, or otherwise dissociated, resulting in a sintered ceramic monolith object. Alternatively, slurry ceramic particles may first be suspended in a liquid and then cast and dried, or cast into a porous mold that removes the liquid, leaving a particulate compact in the mold for further modifications.

Ceramics may also be formed by compacting a dry or slightly damp ceramic powder, with or without an organic binder, in a die or suitable mold. Compaction may be effected with an isostatic pressing technique. It should be understood that a wide array of pressures may be chosen based on such variables as the particular ceramic composition being compacted and the end-use of the particular medical device being formed. For example, pressures may generally range from about 15 psi to about 400,000 psi. In various embodiments of the present technology, the compression of ceramic compositions includes applying an isostatic pressing technique at ambient temperature, or using cold isostatic pressing (CIP). The CIP can use a water or air mixture pressurized up to the desired pressure range of from about 5,000 to about 100,000 psi. In various embodiments, the pressure range is from about 50,000 to about 75,000 psi, or about 60,000 psi.

In various aspects of the present technology, the ceramic compositions comprise ceramic powders. As a non-limiting example, a typical particle size distribution of ceramic powders useful herein may range from about 0.1 µm to about 200 µm in diameter, dependant upon the powder composition and morphology. In various embodiments, the average particle size of ceramic powders for use with ceramic medical devices is less than 10 µm in diameter, less than 5 µm in diameter, or less than 1 µm in diameter. In various embodiments, the ceramic powder may have an average diameter of from about 0.1 µm to about 5 µm. The ceramic powder can be of a substantially homogenous particle size, or can be a mixture of at least two different particle sizes. For example, it may contain a first portion from a first mixture of ceramic particles having a diameter of from about 0.1 µm to about 2 µm and a second portion from a second mixture of ceramic particles having a diameter of from about 2 µm to about 5 µm. The ceramic powder should be substantially free from impurities that could interfere with the forming processes. Appropriately sized and purified particles facilitate successful completion of the processing steps and can prevent or minimize creating a ceramic material that may be susceptible to a crack.

Forming may also comprise compaction of the ceramic compositions of the present technology with other substrates to produce ceramic composites following sintering. As an example, such other substrates may include metal objects, such as metal domes for use with an acetabular shell-type implant as shown in FIG. 1. Nonlimiting examples of metals suitable for composite medical devices may include tantalum, tungsten, cobalt, chromium, titanium, and combinations or alloys thereof.

Alternatively, or in addition, the ceramic compositions of the present technology may further comprise reinforcing materials, for example metal filler. Preferably, the metal is inert to the ceramic, and is biocompatible. Suitable metals may include one or more of tantalum, gold, tungsten, cobalt, chromium, titanium, and alloys thereof. The metal filler can be present in various shapes such as randomly shaped particles, spherical powder, fibers, whiskers, rods, or random shapes. In general, the fillers should have an elongated shape, such as a fiber, for further strengthening and reinforcing of the ceramic. Reinforcing materials may further be continuous in nature. For example, the metal filler of the disclosure may comprise a metal mesh or matrix, or continuous metal filaments or wires that provide reinforcement to the medical device. Reinforcing materials may further include non-metal materials, such as carbon or silica based fillers that do not decompose or dissociate at temperatures sufficient for sintering of ceramics.

In one exemplary method, a green body is formed having a first ceramic composition selected from those described above, such as a ceramic powder or slurry. After an optional sintering step, the green body is reduced to form ceramic fragments. Such a reducing process forms smaller pieces and fragments of controlled geometries. The reducing process may include various mechanical crushing or pulverizing techniques as known in the art in order to obtain ceramic fragments of a desired or predetermined size and/or shape. The ceramic fragments may be sifted, sieved, and/or separated to select the appropriate size particles for use in the outer layer.

In various embodiments, ceramic fragments having a diameter from about 0.1 mm to about 10 mm, from about 1 mm to about 5 mm, and from about 1 mm to about 2 mm are useful with the present technology. As referred to herein, "diameter" refers to the longest dimension of the particles, it being understood that fragments may have irregular shapes without a circular cross sections. Further, it is understood that the ceramic fragments in any given embodiment are likely to have a distribution of particle sizes. For example, the ceramic fragments may have a distribution of sizes wherein at least about 90% of the fragments have a diameter of from about 0.5 mm to about 5 mm, and at least about 25% of the fragments have a diameter of from about 1 to about 2 mm. In some embodiments, the ceramic fragments have a size distribution wherein at least about 50 wt % of the fragments have a diameter from about 0.5 mm to about 2 mm and the remaining fragments have a diameter from about 2 mm to about 5 mm. For example, ceramic fragments have a size distribution wherein about 50 wt % of the fragments have a diameter from about 0.5 mm to about 2 mm and about 50 wt % of the fragments have a diameter from about 2 mm to about 5 mm. In another embodiment, the ceramic fragments are selected having a size distribution wherein about 75 wt % of the fragments have a diameter from about 0.5 mm to about 2 mm and about 25 wt % of the fragments have a diameter from about 2 mm to about 5 mm.

The particle size of the ceramic fragments may vary according to the desired porosity for the final use or application. Without limiting the structure or function of the present implants, it is envisioned that the ceramic-containing outer layer of the implants of the present technology can provide the texture to facilitate interdigitation with existing bone structure. It should be understood that adequate pore size may vary based on the application of the medical device, and pore size may be selectively adjusted according to the process of the disclosure. As nonlimiting examples, pore size for mineralization may be larger than 150 µm, and adequate size for interconnection may be approximately 75 µm. Also, a pore diameter of 200 µm corresponds to the average diameter of an osteon in human bone, while a pore diameter of 500 µm corresponds to remodeled cancellous bone. In various embodiments, pores range in size from about 50 µm to about 600 µm in diameter. Based on the ceramic fragment sizes, an outer layer may have an open cell type structure and can be fabricated to many different desired porosity and pore sizes. Thus, in theory, it may be matched near perfectly with the surrounding natural bone in order to provide an optimal matrix for ingrowth and mineralization. Furthermore, medical devices having metal substrates according to the disclosure may have perforations for promotion of bone ingrowth. Perforations may range in size from about 50 µm to about 600 µm in diameter.

The methods include filling a mold with a second ceramic composition to form a ceramic base, or body. In various aspects, the first and second ceramic compositions have substantially the same chemical composition. For example, if the green body comprises a ceramic powder, the ceramic base may comprise the same ceramic powder. In various aspects, the ceramic base is shaped. The ceramic base is typically provided with a shape operable as a medical implant for an animal (e.g., human) subject. Generally, the ceramic base is molded or shaped prior to the addition of the ceramic fragments (or mixture of ceramic fragments and a ceramic powder) of the outer layer. For example, shaping the composition of the ceramic base may include using a plastic or suitable mandrel to compact or alter the geometry of the ceramic base. In such an embodiment, the ceramic base may be pressed to a predetermined pressure, up to about 10,000 psi. In certain embodiments, the implant may be further shaped or formed later, after the outer layer is added and the assembly is sintered.

Once the ceramic base is optionally shaped or pressed, the reduced ceramic fragments may be added to the ceramic base, preferably in a homogeneous distribution, to form an outer layer. The outer layer may be continuous and cover the entire surface of the ceramic base, or optionally be provided on only a portion or specific region thereof. The ceramic fragment outer layer can be applied having variable properties, such as thickness, texture, porosity, density, and the like. Generally, the outer ceramic fragment layer is uniformly deposited or formed having an average thickness, i.e., normal to the ceramic base surface, of less than about 5 mm. In various embodiments, the outer ceramic fragment layer is formed having an average thickness of from about 1 mm to about 3 mm, or from about 3 mm to about 5 mm.

In certain aspects, a ceramic composition, such as a ceramic powder is mixed with the ceramic fragments to form a mixture, and the mixture is subsequently added to the mold to form the outer layer. In this regard, the ceramic powder may be mixed with the ceramic fragments to form a mixture having a weight ratio of ceramic powder to ceramic fragments of from about 1:5 to about 1:3. In various embodiments, it may be desirable to form the outer layer keeping the larger ceramic particles near the surface. This provides a higher amount of surface area that may potentially be available for bone ingrowth or other chemical or deposition processes.

Once the ceramic fragments are added to the mold forming an outer layer over at least a portion of the ceramic base, pressure is applied to the mold to compress the outer layer onto the ceramic base and to form a green assembly. As used herein, a "green assembly" refers to the combination of the ceramic base and the outer layer. The pressure applied to the mold may include using an isostatic pressing technique to compress the green assembly at a pressure of from about 50,000 to about 75,000 psi, or about 60,000 psi. As previously described, certain of the ceramic fragments or particles of the outer layer may be partially embedded within or pressed into the ceramic base. This may provide for enhanced union between the outer layer and ceramic base. In other aspects, the applied pressure compresses and secures the outer layer onto the base layer, however, the ceramic fragments are not pressed into the base.

Once the green assembly is formed having a ceramic base and porous outer layer, it is sintered for strength, density, and/or rigidity. Note that in certain embodiments, the green body may be sintered prior to reducing it to ceramic fragments, thereby forming sintered ceramic fragments used in the outer layer. In effect, this would provide the ceramic fragments being subjected to a sintering process two times. The sintering process can be performed at once or in stages. The temperature can be increased and decreased in a furnace or chamber (by 2° C., 5° C., 10° C., 20° C., 50° C., for example) at time intervals (from 5 seconds to 15 minutes, for example). Once the desired temperature or "hold temperature" is reached, which may vary for the particular ceramics, the component is maintained at the hold temperature from about 1 hour to about 20 hours. Hold temperatures may be from about 700° C. to about 2,000° C. In certain embodiments, the green assembly (or green body, if desired) is sintered at a temperature of about 1,750° C. for about 15 hours. In various aspects, the step of sintering the green assembly includes sintering adjacent particles of the ceramic composition of the base to one another, sintering the ceramic fragments of the outer layer to one another, and concurrently sintering the outer layer to the ceramic base, providing an integral subassembly. Alternative methods for sintering can also be used, such as those disclosed in U.S. patent application Ser. No. 11/595,134 filed Nov. 10, 2006 and published as U.S. Patent Application Publication No. 2008/0114468, Kumar, published May 15, 2008, which is incorporated by reference herein in its entirety.

In certain aspects and methods of the present technology, rather than using ceramic fragments to form an outer layer, a porous ceramic powder outer layer may be applied using conventional secondary treatments, including plasma spraying processes and techniques as are known in the art. Further surface texturing may include various mechanical, chemical, or optical modifications, if desired.

In various embodiments, where the outer layer comprises a coating resulting from porous plasma spray treatment, a green ceramic base can be placed in a suitable plasma spray system where the outer layer is plasma sprayed with a desired ceramic powder to generate a rough, or porous, outer surface texture. For implants requiring an articulating surface, portions may be polished to an acceptable roughness, for example less than 0.1 micron Ra, to provide the articulating surface. Once the green ceramic base is coated with a porous outer layer, it may be sintered as described above.

It may be desirable to deposit a layer of metal, such as titanium or a titanium alloy, over at least a portion of the rough surface texture of the implant. Specialized techniques such as ion beam enhanced deposition (IBED) may be used to provide such a layer with the present technology. U.S. Pat. No. 5,055,318, Deutchman et al., issued Oct. 8, 1991 provides various process details and is incorporated by reference herein. In certain embodiments, an ion beam enhanced deposition technique may be used to deposit a layer of metal over a portion of the rough surface of the implant, and a porous metallic layer may be deposited over at least a portion of the metal layer using a porous plasma spray technique.

In other aspects and methods of the present technology, the outer layer is provided initially including ceramic fragments and/or ceramic powder along with a spacing agent. The spacing agent, or porogen particles, of the outer layer may be used to provide a desired porosity. The spacing agent can be removable from the outer layer, for example during sintering or by another application of heat, and it may be desirable that the spacing agent does not leave residue in the porous outer layer. After the spacing agent decomposes, pores or gaps remain between the ceramic fragments, particles, or powder where the spacing agent was located. It may be further desirable that the spacing agent expands or contracts to supplement the formation of pores of a desired size within the outer layer. The pores may range in size of from between about 1 to about 1,000 micrometers, or as otherwise desired. For example, in certain embodiments, it may be desirable to have a pore size from about 100 to about 600 micrometers. In other embodiments, it may be desirable to have a pore size from between about 500 to about 700 micrometers. The spacing agent can be selected from the group consisting of hydrogen peroxide, urea, ammonium bicarbonate, ammonium carbonate, ammonium carbamate, calcium hydrogen phosphate, naphthalene, and mixtures thereof, or can be any other suitable subliming and space forming material. Generally, the spacing agent has a melting point, boiling point, or sublimation temperature, of less than about 400° C., or less than about 350° C., depending on the specific materials used.

The present technology is not limited to providing only a first ceramic outer coating. For example, calcium phosphate phases (CPP) can be deposited directly to the rough ceramic outer layer, or can be further applied onto portions thereof to improve bioinert behavior of implant materials. Calcium phosphate phases may have a lot of bioactive potential, thus enabling chemical bonding to natural bone. As used herein, the main inorganic constituent CPP may contain amorphous calcium phosphate ($Ca_9(PO_4)_6 \cdot nH_2O$), hydroxyapatite ($Ca_{10}(PO_4)_6(OH)_2$), octacalcium phosphate ($Ca_8H_2(PO)_6H_2O$), or brushite ($CaHPO_4 \cdot 2H_2O$), or mixtures thereof. The CPP can additionally be doped with ions such as fluoride, silver, magnesium, carbonate, strontium, or sodium.

As is known in the art, hydroxyapatite ($Ca_{10}(PO_4)_6(OH)_2$) is a CPP biocompatible material that is similar in composition to the major inorganic mineral content of natural bone. As such, hydroxyapatite coatings provided on ceramic implants can enhance an implant's osteoconductivity potential, among other things. Common deposition techniques for coating hydroxyapatite onto implants can include plasma spray coating, electrochemical deposition, and sol-gel deposition. One advantage of using such deposition processes is that they are not "line of sight" processes and thus can provide a complete coating coverage of complex shaped substrates.

The roughened ceramic can be used for a variety of applications in orthopedic and dental reconstruction applications. In certain aspects, a biocompatible porous metallic layer, such as a titanium alloy, can be deposited on the outer surface of the ceramic device using a plasma spray process with the objective of enhancing apposition of surrounding bone tissue to the ceramic implant. The roughened surface on the ceramic implant may help in providing micromechanical stability at the ceramic-metal coating interface, which in turn may enhance the adhesion of the metal coating to the ceramic implant.

In various embodiments, optional agents can be coated onto or in a surface of the outer ceramic coating component of the implant. For example, a coated implant may additionally be placed in an antibiotic solution where it adsorbs at least one antibiotic or other optional material into the porous ceramic coating. Further optional materials may include bone materials, blood products, bioactive materials, additional ceramics, polymers, and combinations thereof. Bone materials include bone powder and demineralized bone. Blood products include blood fractions and other blood derived materials, such as platelet rich plasma. Bioactive agents useful herein include organic molecules, proteins, peptides, peptidomimetics, nucleic acids, nucleoproteins, antisense molecules, polysaccharides, glycoproteins, lipoproteins, carbohydrates and polysaccharides, botanical extracts, and synthetic and biologically engineered analogs thereof, living cells such as stem cells (e.g., adipose derived stem cells) chondrocytes, bone marrow cells, viruses and virus particles, natural extracts, and combinations thereof. Specific examples of bioactive materials include hormones, antibiotics and other antiinfective agents, hematopoietics, thrombopoietics, agents, antiviral agents, antiinflammatory agents, anticoagulants, therapeutic agents for osteoporosis, enzymes, vaccines, immunological agents and adjuvants, cytokines, growth factors, cellular attractants and attachment agents, gene regulators, vitamins, minerals and other nutritionals, nutraceuticals and combinations thereof. Additional ceramics include resorbable or non-resorbable ceramic materials, such as glasses or ceramics comprising mono-, di-, tri-, α-tri-, β-tri-, and tetra-calcium phosphate, calcium sulfates, calcium oxides, calcium carbonates, magnesium calcium phosphates, phosphate glass, bioglass, and mixtures thereof. Additional polymers include resorbable or non-resorbable polymers, such as polyhydroxyalkanoates, polylactones and their copolymers. In various embodiments, the optional material may be a resorbable ceramic, resorbable polymer, antimicrobial, demineralized bone, blood product, stem cell, growth factor or mixture thereof. Preferably, the optional material(s) assist or facilitate in-growth of new tissue into the medical implant.

The medical implant can be an orthopedic implant, for example, an acetubular cup, a knee implant, a shoulder implant, a femoral implant or femoral resurfacing system, a dental implant, a bone fixation device, scaffold, and the like. The medical implant can also be custom made or a generic shape for filling in a bone defect caused by surgical intervention or disease. As referenced above, "implant" may refer to an entire implant as a whole, or a portion thereof; portions may be as large or as small as necessary to accommodate the specific need.

The implant can also be attached as part of an orthopedic insert, such as those disclosed in U.S. patent application Ser. No. 12/038,570 filed Feb. 27, 2008 and published as U.S. Patent Application Publication No. 2008/0147187, Bollinger et al., published Jun. 19, 2008, which is incorporated by reference herein in its entirety. The implant can also be used to form a geostructure, which is a three-dimensional geometric porous engineered structure that is self supporting and is constructed of rigid filaments joined together to form regular or irregular geometric shapes. The structure is described in more detail in U.S. Pat. No. 6,206,924, Timm, issued Mar. 27, 2001, which is incorporated by reference.

The embodiments described herein are exemplary and not intended to be limiting in describing the full scope of compositions and methods of the present technology. Equivalent changes, modifications and variations of embodiments, materials, compositions and methods can be made within the scope of the present technology, with substantially similar results.

Non-Limiting Discussion of Terminology:

The headings (such as "Introduction" and "Summary") and sub-headings used herein are intended only for general organization of topics within the present disclosure, and are not intended to limit the disclosure of the technology or any aspect thereof. In particular, subject matter disclosed in the "Introduction" may include novel technology and may not constitute a recitation of prior art. Subject matter disclosed in the "Summary" is not an exhaustive or complete disclosure of the entire scope of the technology or any embodiments thereof. Classification or discussion of a material within a section of this specification as having a particular utility is made for convenience, and no inference should be drawn that the material must necessarily or solely function in accordance with its classification herein when it is used in any given composition.

The description and specific examples, while indicating embodiments of the technology, are intended for purposes of illustration only and are not intended to limit the scope of the technology. Moreover, recitation of multiple embodiments having stated features is not intended to exclude other embodiments having additional features, or other embodiments incorporating different combinations of the stated features. Specific examples are provided for illustrative purposes of how to make and use the compositions and methods of this technology and, unless explicitly stated otherwise, are not intended to be a representation that given embodiments of this technology have, or have not, been made or tested.

As used herein, the words "desire" or "desirable" refer to embodiments of the technology that afford certain benefits, under certain circumstances. However, other embodiments may also be desirable, under the same or other circumstances. Furthermore, the recitation of one or more desired embodiments does not imply that other embodiments are not useful, and is not intended to exclude other embodiments from the scope of the technology.

As used herein, the word "include," and its variants, is intended to be non-limiting, such that recitation of items in a list is not to the exclusion of other like items that may also be useful in the materials, compositions, devices, and methods of this technology. Similarly, the terms "can" and "may" and their variants are intended to be non-limiting, such that recitation that an embodiment can or may comprise certain elements or features does not exclude other embodiments of the present technology that do not contain those elements or features.

Although the open-ended term "comprising," as a synonym of non-restrictive terms such as including, containing, or having, is used herein to describe and claim embodiments of the present technology, embodiments may alternatively be described using more limiting terms such as "consisting of" or "consisting essentially of." Thus, for any given embodiment reciting materials, components or process steps, the present technology also specifically includes embodiments consisting of, or consisting essentially of, such materials, components or processes excluding additional materials, components or processes (for consisting of) and excluding additional materials, components or processes affecting the significant properties of the embodiment (for consisting essentially of), even though such additional materials, components or processes are not explicitly recited in this application. For example, recitation of a composition or process reciting elements A, B and C specifically envisions embodiments consisting of, and consisting essentially of, A, B and C, excluding an element D that may be recited in the art, even though element D is not explicitly described as being excluded herein.

As referred to herein, all compositional percentages are by weight of the total composition, unless otherwise specified. Disclosures of ranges are, unless specified otherwise, inclusive of endpoints. Thus, for example, a range of "from A to B" or "from about A to about B" is inclusive of A and of B. Disclosure of values and ranges of values for specific parameters (such as temperatures, molecular weights, weight percentages, etc.) are not exclusive of other values and ranges of values useful herein. It is envisioned that two or more specific exemplified values for a given parameter may define endpoints for a range of values that may be claimed for the parameter. For example, if Parameter X is exemplified herein to have value A and also exemplified to have value Z, it is envisioned that Parameter X may have a range of values from about A to about Z. Similarly, it is envisioned that disclosure of two or more ranges of values for a parameter (whether such ranges are nested, overlapping or distinct) subsume all possible combination of ranges for the value that might be claimed using endpoints of the disclosed ranges. For example, if Parameter X is exemplified herein to have values in the range of 1-10, or 2-9, or 3-8, it is also envisioned that Parameter X may have other ranges of values including 1-9, 1-8, 1-3, 1-2, 2-10, 2-8, 2-3, 3-10, and 3-9.

When an element or layer is referred to as being "on", "engaged to", "connected to" or "coupled to" another element or layer, it may be directly on, engaged, connected or coupled to the other element or layer, or intervening elements or layers may be present. In contrast, when an element is referred to as being "directly on", "directly engaged to", "directly connected to" or "directly coupled to" another element or layer, there may be no intervening elements or layers present. Other words used to describe the relationship between elements should be interpreted in a like fashion (e.g., "between" versus "directly between," "adjacent" versus "directly adjacent," etc.). As used herein, the term "and/or" includes any and all combinations of one or more of the associated listed items.

What is claimed is:

1. A method for forming a ceramic implant having a rough surface texture, the method comprising:
   a. forming a green body of a first ceramic composition;
   b. reducing the green body thereby forming ceramic fragments;
   c. filling a mold with a second ceramic composition and compressing the second ceramic composition to a predetermined pressure to form a ceramic base;
   d. adding the ceramic fragments to the mold and forming an outer layer over at least a portion of the ceramic base;
   e. applying pressure to the mold to compress the outer layer onto the ceramic base and to form a green assembly; and
   f. sintering the green assembly to form a ceramic implant having a rough surface texture.

2. The method of claim 1, wherein a ceramic powder is mixed with the ceramic fragments to form a mixture and the mixture is added to the mold to form the outer layer.

3. The method of claim 2, wherein the mixture comprises a weight ratio of ceramic powder to ceramic fragments from about 1:5 to about 1:3.

4. The method of claim 1, wherein a spacing agent is mixed with the ceramic fragments of the outer layer and the spacing agent is removed during sintering the green assembly.

5. The method of claim 1, further comprising sifting the ceramic fragments and selecting a desired particle size from about 0.5 mm to about 5 mm for use in forming the outer layer.

6. The method of claim 1, wherein at least one of the first and second ceramic compositions comprises a ceramic powder having an average particle diameter from about 0.1 μm to about 5 μm.

7. The method of claim 1, wherein the ceramic fragments have a size distribution wherein at least about 90% of the fragments have a diameter of from about 0.5 mm to about 5 mm, and at least about 25% of the fragments have a diameter of from about 1 mm to about 2 mm.

8. The method of claim 7, wherein the ceramic fragments are selected having a size distribution wherein about 75 wt % of the fragments have a diameter from about 1 mm to about 2 mm and about 25 wt % of the fragments have a diameter from about 2 mm to about 5 mm.

9. The method of claim 7, wherein the ceramic fragments are selected having a size distribution wherein about 50 wt % of the fragments have a diameter from about 1 mm to about 2 mm and about 50 wt % of the fragments have a diameter from about 2 mm to about 5 mm.

10. The method of claim 1, wherein applying pressure to the mold comprises using an isostatic pressing technique to compress the green assembly to a pressure of from about 50,000 to about 75,000 psi.

11. The method of claim 1, wherein applying pressure to the mold comprises pressing a plurality of the ceramic fragments into the ceramic base.

12. The method of claim 1, further comprising sintering the ceramic fragments prior to adding the ceramic fragments to the mold.

13. The method of claim 1, wherein the first and second ceramic compositions have substantially the same chemical composition.

14. The method of claim 1, wherein at least one of the first and second ceramic compositions comprises a ceramic selected from the group consisting of alumina, zirconia, metal nitride, metal carbide, and mixtures thereof.

15. The method of claim 1, further comprising shaping the ceramic base prior to adding the ceramic fragments to the mold and forming the outer layer.

16. The method of claim 15, wherein shaping the ceramic base comprises using a mandrel to shape and press the second ceramic composition.

17. The method of claim 1, further comprising depositing a porous metallic layer over at least a portion of the rough surface texture of the ceramic implant.

18. The method of claim 17, wherein the porous metallic layer comprises a titanium alloy.

19. The method of claim 1, further comprising depositing a layer of a titanium alloy over at least a portion of the rough surface texture of the implant using an ion beam enhanced deposition technique and further depositing a porous metallic layer over at least a portion of the titanium alloy layer using a porous plasma spray technique.

20. A method for forming a ceramic implant having a rough surface texture, the method comprising:
   a. filling a mold with a ceramic composition and compressing the ceramic composition to a predetermined pressure to form a ceramic base;
   b. adding ceramic fragments to the mold and forming an outer layer over at least a portion of the ceramic base;
   c. applying pressure of from about 50,000 to about 75,000 psi to the mold to compress the outer layer onto the ceramic base and to form a green assembly; and
   d. sintering the green assembly to form a ceramic implant having a rough surface texture.

* * * * *